(12) United States Patent
Chowaniec et al.

(10) Patent No.: US 10,420,577 B2
(45) Date of Patent: Sep. 24, 2019

(54) APPARATUS AND METHOD FOR TISSUE THICKNESS SENSING

(71) Applicant: Covidien LP, Mansfield, MA (US)

(72) Inventors: David Chowaniec, Rocky Hill, CT (US); Matthew Chowaniec, Middletown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/565,503

(22) Filed: Dec. 10, 2014

(65) Prior Publication Data

US 2015/0272604 A1    Oct. 1, 2015

Related U.S. Application Data

(60) Provisional application No. 61/972,511, filed on Mar. 31, 2014.

(51) Int. Cl.
*A61B 17/295* (2006.01)
*A61B 17/068* (2006.01)
(Continued)

(52) U.S. Cl.
CPC .......... *A61B 17/295* (2013.01); *A61B 17/068* (2013.01); *A61B 17/07207* (2013.01); *A61B 17/2909* (2013.01); *A61B 34/25* (2016.02); *A61B 90/10* (2016.02); *A61B 17/28* (2013.01); *A61B 2017/00017* (2013.01);
(Continued)

(58) Field of Classification Search
CPC ..... A61B 17/068; A61B 17/28; A61B 17/295; A61B 2017/00017; A61B 2017/00022; A61B 2017/00039; A61B 2017/00115; A61B 2017/0023; A61B 2017/00398; A61B 2017/0046; A61B 2017/00464;
(Continued)

(56) References Cited

U.S. PATENT DOCUMENTS

| 4,346,434 A | 8/1982 | Morinaga |
| 4,486,176 A | 12/1984 | Tardieu et al. |

(Continued)

FOREIGN PATENT DOCUMENTS

| AU | 2013270535 A1 | 1/2014 |
| CN | 103340659 A | 10/2013 |

(Continued)

OTHER PUBLICATIONS

European Search Report for EP 15161597.8 dated Aug. 3, 2015.
(Continued)

*Primary Examiner* — Devin B Henson (57) ABSTRACT

A surgical instrument is provided. The surgical instrument includes: a test end effector including a test jaw assembly having a pair of jaws configured to clamp about tissue and at least one sensor configured to measure at least one tissue property; and a handle assembly configured to couple to the treatment end effector. The handle assembly includes: a drive assembly; a motor operatively coupled to the drive assembly; and a controller operatively coupled to the motor, the controller configured to control operation of the motor to actuate the test end effector to measure the at least one tissue property and to determine, based on the at least one tissue property, at least one suitable treatment end effector.

11 Claims, 10 Drawing Sheets

(51) Int. Cl.
*A61B 17/29* (2006.01)
*A61B 34/00* (2016.01)
*A61B 17/28* (2006.01)
*A61B 17/00* (2006.01)
*A61B 90/00* (2016.01)
*A61B 17/072* (2006.01)
*A61B 90/10* (2016.01)
*A61B 90/30* (2016.01)

(52) U.S. Cl.
CPC ........... *A61B 2017/00022* (2013.01); *A61B 2017/0023* (2013.01); *A61B 2017/00026* (2013.01); *A61B 2017/00084* (2013.01); *A61B 2017/00115* (2013.01); *A61B 2017/00353* (2013.01); *A61B 2017/00398* (2013.01); *A61B 2017/00464* (2013.01); *A61B 2017/00477* (2013.01); *A61B 2017/00734* (2013.01); *A61B 2017/0725* (2013.01); *A61B 2017/2925* (2013.01); *A61B 2017/2926* (2013.01); *A61B 2017/2931* (2013.01); *A61B 2034/256* (2016.02); *A61B 2090/061* (2016.02); *A61B 2090/065* (2016.02); *A61B 2090/0807* (2016.02); *A61B 2090/309* (2016.02)

(58) Field of Classification Search
CPC .... A61B 2017/0725; A61B 2017/2926; A61B 2017/2931
See application file for complete search history.

(56) References Cited

U.S. PATENT DOCUMENTS

| | | | |
|---|---|---|---|
| 5,115,174 A | 5/1992 | Masuda et al. | |
| 5,383,880 A | 1/1995 | Hooven | |
| 5,469,215 A | 11/1995 | Nashiki | |
| 5,533,521 A | 7/1996 | Granger | |
| 5,543,695 A | 8/1996 | Culp et al. | |
| 6,060,850 A | 5/2000 | Sakabe | |
| 6,159,146 A | 12/2000 | El Gazayerli | |
| 6,352,532 B1 | 3/2002 | Kramer et al. | |
| 6,377,008 B1 | 4/2002 | Hirata | |
| 6,432,065 B1 | 8/2002 | Burdorff et al. | |
| 6,556,778 B2 | 4/2003 | Zhang et al. | |
| 6,680,595 B2 | 1/2004 | Ito | |
| 6,793,652 B1 | 9/2004 | Whitman et al. | |
| 6,846,307 B2 | 1/2005 | Whitman et al. | |
| 6,846,308 B2 | 1/2005 | Whitman et al. | |
| 6,981,941 B2 | 1/2006 | Whitman et al. | |
| 7,023,159 B2 | 4/2006 | Gorti et al. | |
| 7,032,798 B2 | 4/2006 | Whitman et al. | |
| 7,122,982 B2 | 10/2006 | Sasaya et al. | |
| 7,177,533 B2 | 2/2007 | McFarlin et al. | |
| 7,193,376 B2 | 3/2007 | Negoro et al. | |
| 7,416,101 B2 | 8/2008 | Shelton, IV et al. | |
| 7,432,677 B2 | 10/2008 | Heydt et al. | |
| 7,464,847 B2 | 12/2008 | Viola et al. | |
| 7,568,603 B2 | 8/2009 | Shelton, IV et al. | |
| 7,717,312 B2 | 5/2010 | Beetel | |
| 7,755,310 B2 | 7/2010 | West et al. | |
| 7,911,168 B2 | 3/2011 | Koike | |
| 7,994,746 B2 | 8/2011 | Chiu et al. | |
| 8,012,170 B2 | 9/2011 | Whitman et al. | |
| 8,074,731 B2 | 12/2011 | Iwata et al. | |
| 8,089,226 B2 | 1/2012 | Matsutani et al. | |
| 8,968,276 B2 | 3/2015 | Zemlok | |
| 2003/0073981 A1 | 4/2003 | Whitman et al. | |
| 2005/0192609 A1 | 9/2005 | Whitman et al. | |
| 2007/0001636 A1 | 1/2007 | Murphree | |
| 2007/0085496 A1 | 4/2007 | Philipp et al. | |
| 2009/0012556 A1* | 1/2009 | Boudreaux | A61B 17/068 606/206 |
| 2009/0090763 A1* | 4/2009 | Zemlok | A61B 17/07207 227/175.2 |
| 2010/0244757 A1 | 9/2010 | Tsai et al. | |
| 2011/0080132 A1 | 4/2011 | Ogasawara et al. | |
| 2011/0125138 A1* | 5/2011 | Malinouskas | A61B 17/068 606/1 |
| 2011/0155781 A1 | 6/2011 | Swensgard et al. | |
| 2011/0224668 A1* | 9/2011 | Johnson | A61B 18/1233 606/42 |
| 2011/0234132 A1 | 9/2011 | Norell | |
| 2011/0253765 A1 | 10/2011 | Nicholas et al. | |
| 2011/0279072 A1 | 11/2011 | Shimizu et al. | |
| 2012/0116379 A1* | 5/2012 | Yates | A61B 17/00234 606/33 |
| 2012/0138658 A1* | 6/2012 | Ullrich | A61B 17/072 227/175.1 |
| 2012/0211542 A1 | 8/2012 | Racenet | |
| 2013/0146638 A1* | 6/2013 | Mandakolathur Vasudevan | A61B 17/072 227/175.1 |
| 2014/0249557 A1* | 9/2014 | Koch, Jr. | A61B 17/32002 606/170 |

FOREIGN PATENT DOCUMENTS

| | | |
|---|---|---|
| EP | 1974676 A1 | 10/2008 |
| EP | 2044890 A1 | 4/2009 |
| EP | 2491872 A1 | 8/2012 |
| JP | 2008272457 A | 11/2008 |
| JP | 2009090113 A | 4/2009 |
| JP | 2012170820 A | 9/2012 |

OTHER PUBLICATIONS

Chinese Office Action dated Jun. 27, 2018 issued in corresponding CN Application No. 2015101493689.
European Examination Report dated Jun. 21, 2018 issued in corresponding EP Appln. No. 15161597.8.
Chinese Office Action dated Feb. 3, 2019 issued in corresponding CN Appln. No. 2015101493689.
Australian Examination Report dated Feb. 8, 2019 issued in corresponding AU Appln. No. 2015200535.
Japanese Office Action dated Nov. 12, 2018 issued in corresponding JP Appln. No. 2015-050740.
Chinese Office Action dated Jun. 18, 2019 issued in corresponding CN Appln. No. 2015101493689.

* cited by examiner

APPARATUS AND METHOD FOR TISSUE THICKNESS SENSING

CROSS-REFERENCE TO RELATED APPLICATIONS

This application claims the benefit of and priority to U.S. Provisional Patent Application No. 61/972,511, filed Mar. 31, 2014, the entire disclosure of which is incorporated by reference herein.

BACKGROUND

1. Technical Field

The present disclosure relates to surgical apparatus, devices and/or systems for performing endoscopic surgical procedures and methods of use thereof. More specifically, the present disclosure relates to electromechanical, hand-held surgical apparatus, devices and/or systems configured for use with removable disposable end effectors and/or single use end effectors for clamping, cutting and/or stapling tissue.

2. Background of the Related Art

A number of surgical device manufacturers have developed product lines with proprietary drive systems for operating and/or manipulating electromechanical surgical devices. In many instances the electromechanical surgical devices include a reusable handle assembly, and disposable or single use end effectors. The end effectors are selectively connected to the handle assembly prior to use and then disconnected from the handle assembly following use in order to be disposed of or in some instances sterilized for re-use.

Many of these electromechanical surgical devices include complex drive components that utilize a variety of user interfaces that accept user inputs (e.g., controls) for controlling the devices as well as provide feedback to the user. To prevent actuation of drive mechanisms beyond mechanical limits, various switches and sensors are used to detect operational state of the surgical devices.

A variety of end effectors are usable with reusable handle assemblies. However, in certain applications it may be difficult for a practitioner to select a suitable end effector for a specific procedure (e.g., selecting an end effector having fasteners of sufficient length to secure tissue). Accordingly, there is a need for systems and apparatus configured to determine tissue properties and indicate to the practitioner one or more suitable end effectors to treat the tissue.

SUMMARY

According to one embodiment of the present disclosure a surgical instrument is provided. The surgical instrument includes: a test end effector including a test jaw assembly having a pair of jaws configured to clamp about tissue and at least one sensor configured to measure at least one tissue property; and a handle assembly configured to couple to the test end effector. The handle assembly includes: a drive assembly; a motor operatively coupled to the drive assembly; and a controller operatively coupled to the motor, the controller configured to control operation of the motor to actuate the test end effector to measure the at least one tissue property and to determine, based on the at least one tissue property, at least one suitable treatment end effector.

According to one aspect of the above embodiment, the at least one sensor is configured to measure pressure exerted on the tissue. The at least one sensor is selected from the group consisting of force transducers, piezoelectric elements, piezoresistive elements, load cells, metal film strain gauges, semiconductor strain gauges, inductive pressure sensors, capacitive pressure sensors, potentiometric pressure transducers, and combinations thereof.

According to another aspect of the above embodiment, the handle assembly includes a user interface device coupled to the controller. The user interface device is selected from the group consisting of a light emitting diode, an audio device, a display, and combinations thereof. The user interface device outputs an indicia corresponding to the at least one suitable treatment end effector.

According to one embodiment of the present disclosure a surgical system is provided. The surgical system includes: a test end effector including at least one sensor configured to measure at least one tissue property; a plurality of treatment end effectors, each of the treatment end effectors including a jaw assembly having a pair of jaws configured to clamp about tissue; and a handle assembly configured to selectively couple to at least one of the treatment end effector or a test end effector. The handle assembly includes: a drive assembly; a motor operatively coupled to the drive assembly; and a controller operatively coupled to the motor, the controller configured to control operation of the motor to actuate the test end effector to measure the at least one tissue property and to indicate at least one suitable treatment end effector from the plurality of treatment end effectors based on the at least one tissue property.

According to one aspect of the above embodiment, the at least one sensor is configured to measure pressure exerted on the tissue. The at least one sensor is selected from the group consisting of force transducers, piezoelectric elements, piezoresistive elements, load cells, metal film strain gauges, semiconductor strain gauges, inductive pressure sensors, capacitive pressure sensors, potentiometric pressure transducers, and combinations thereof.

According to another aspect of the above embodiment, the handle assembly includes a user interface device coupled to the controller. The user interface device is selected from the group consisting of a light emitting diode, an audio device, a display, and combinations thereof. The user interface device outputs an indicia corresponding to the at least one suitable treatment end effector.

According to a further aspect of the above embodiment a method for treating tissue, is provided. The method includes: coupling a test end effector to a handle assembly, the test end effector including at least one sensor configured to measure at least one tissue property; actuating the test end effector to measure the at least one tissue property; and determining based on the at least one tissue property at least one suitable treatment end effector.

According to one aspect of the above embodiment, the method further includes: indicating the at least one suitable treatment end effector on a user interface of the handle assembly. Indicating on the user interface includes outputting an indicia corresponding to the at least one suitable treatment end effector, wherein indicia is selected from the group consisting of a color, an identification number, an audio tone, and combinations thereof.

According to another aspect of the above embodiment, the method further includes: coupling the at least one suitable treatment end effector to the handle assembly; and clamping tissue with the at least one suitable treatment end effector.

According to a further aspect of the above embodiment, the method further includes: actuating the test end effector includes measuring pressure exerted on the tissue.

DESCRIPTION OF THE DRAWINGS

Embodiments of the present disclosure are described herein with reference to the accompanying drawings, wherein.

DETAILED DESCRIPTION

A surgical system, in accordance with an embodiment of the present disclosure, is generally designated as 10, and is in the form of a powered hand held electromechanical instrument configured for selective attachment thereto of a plurality of different end effectors that are each configured for actuation and manipulation by the powered hand held electromechanical surgical instrument.

Figure 1:
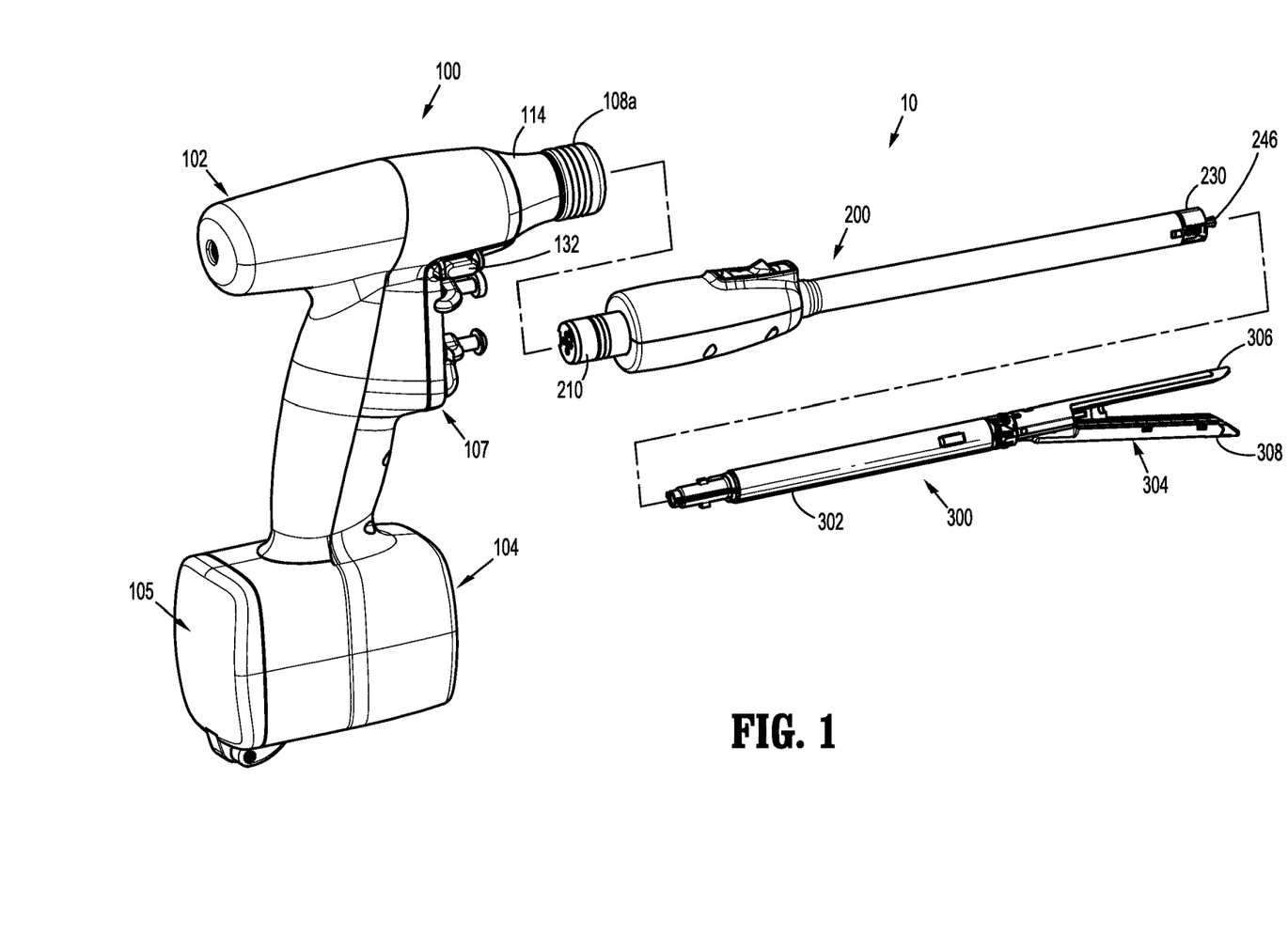
FIG. 1 is a perspective, disassembled view of an electromechanical surgical system including a surgical instrument, an adapter, and an end effector, according to the present disclosure.

As illustrated in FIG. 1, surgical instrument 100 is configured for selective connection with an adapter 200, and, in turn, adapter 200 is configured for selective connection with an end effector or single use loading unit 300.

Figure 2:
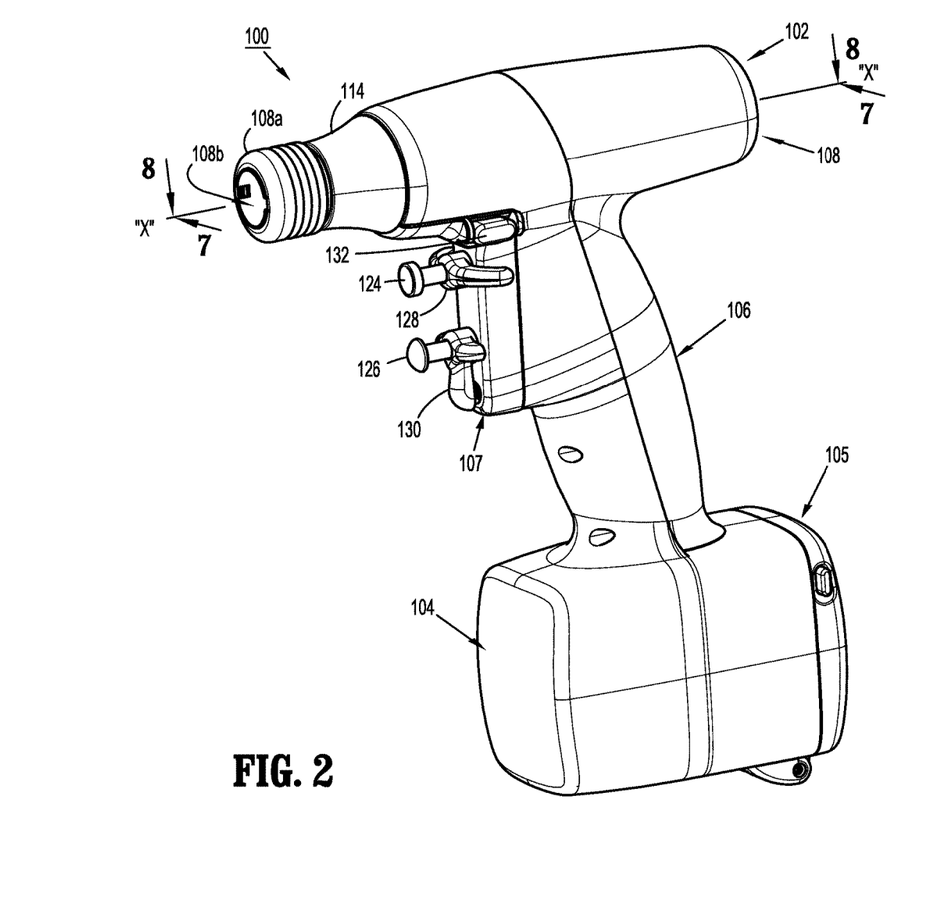
FIG. 2 is a perspective view of the surgical instrument of FIG. 1, according to the present disclosure.
Figure 3:
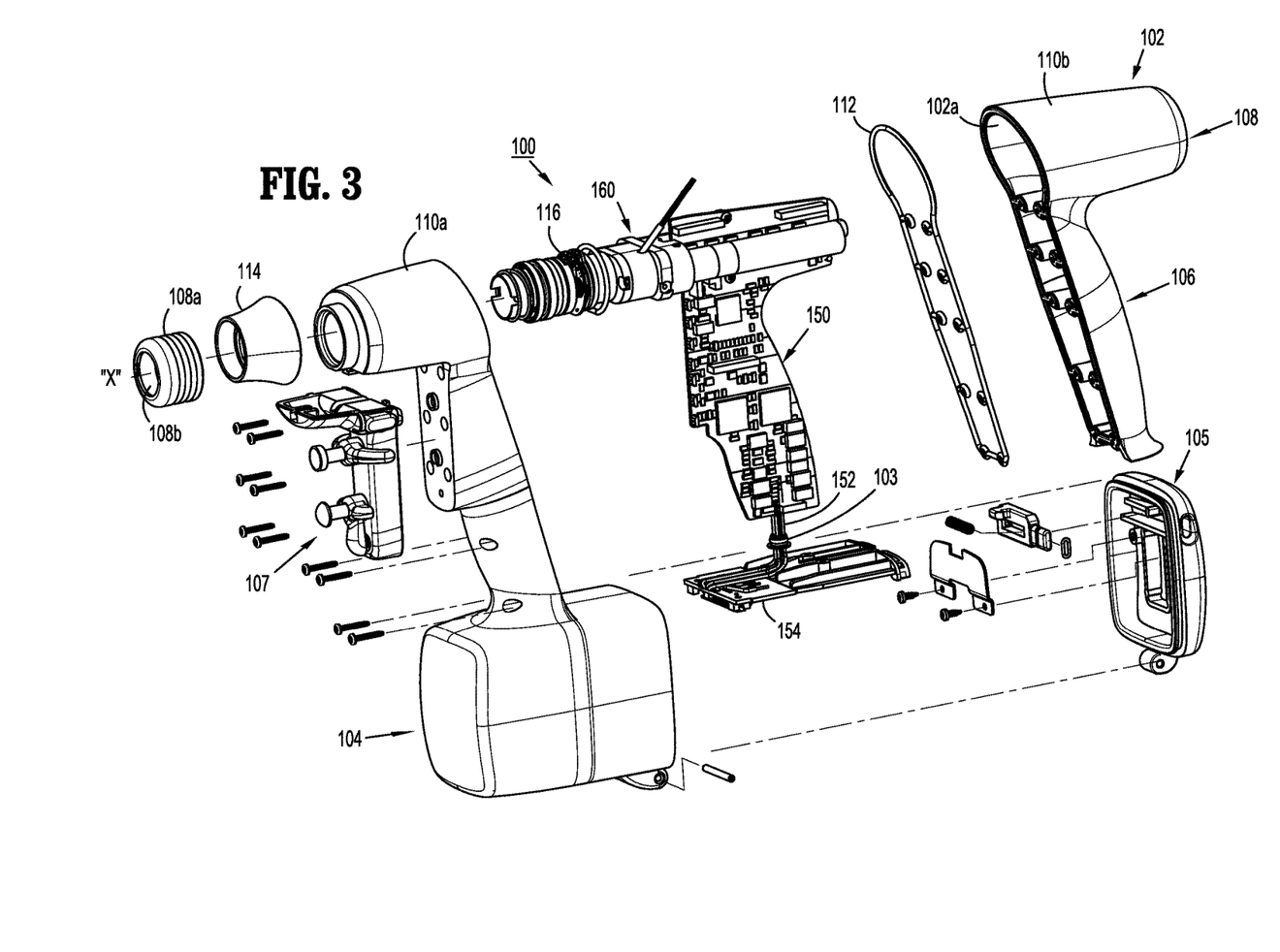
FIG. 3 is perspective, exploded view of the surgical instrument of FIG. 1, according to the present disclosure.

As illustrated in FIGS. 1-3, surgical instrument 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners. When joined, distal and proximal half-sections 110a, 110b define a handle housing 102 having a cavity 102a therein in which a circuit board 150 and a drive mechanism 160 are situated.

Distal and proximal half-sections 110a, 110b are divided along a plane that traverses a longitudinal axis "X" of upper housing portion 108, as seen in FIGS. 2 and 3. Handle housing 102 includes a gasket 112 extending completely around a rim of distal half-section and/or proximal half-section 110a, 110b and being interposed between distal half-section 110a and proximal half-section 110b. Gasket 112 seals the perimeter of distal half-section 110a and proximal half-section 110b. Gasket 112 functions to establish an air-tight seal between distal half-section 110a and proximal half-section 110b such that circuit board 150 and drive mechanism 160 are protected from sterilization and/or cleaning procedures.

In this manner, the cavity 102a of handle housing 102 is sealed along the perimeter of distal half-section 110a and proximal half-section 110b yet is configured to enable easier, more efficient assembly of circuit board 150 and a drive mechanism 160 in handle housing 102.

Intermediate housing portion 106 of handle housing 102 provides a housing in which circuit board 150 is situated. Circuit board 150 is configured to control the various operations of surgical instrument 100, as will be set forth in additional detail below.

Lower housing portion 104 of surgical instrument 100 defines an aperture (not shown) formed in an upper surface thereof and which is located beneath or within intermediate housing portion 106. The aperture of lower housing portion 104 provides a passage through which wires 152 pass to electrically interconnect electrical components (a power source 156, as illustrated in FIG. 4, a circuit board 154, as illustrated in FIG. 3, etc.) situated in lower housing portion 104 with electrical components (circuit board 150, drive mechanism 160, etc.) situated in intermediate housing portion 106 and/or upper housing portion 108.

Handle housing 102 includes a gasket 103 disposed within the aperture (not shown) of lower housing portion 104 thereby plugging or sealing the aperture of lower housing portion 104 while allowing wires 152 to pass therethrough. Gasket 103 functions to establish an air-tight seal between lower housing portion 106 and intermediate housing portion 108 such that circuit board 150 and drive mechanism 160 are protected from sterilization and/or cleaning procedures.

As shown, lower housing portion 104 of handle housing 102 provides a housing in which a rechargeable power source 156 (FIG. 4), is removably situated. Power source 156 is configured to supply power to any of the electrical components of surgical instrument 100. Lower housing portion 104 defines a cavity (not shown) into which power source 156 is inserted. Lower housing portion 104 includes a door 105 pivotally connected thereto for closing cavity of lower housing portion 104 and retaining power source 156 therein.

Figures 4, 5:
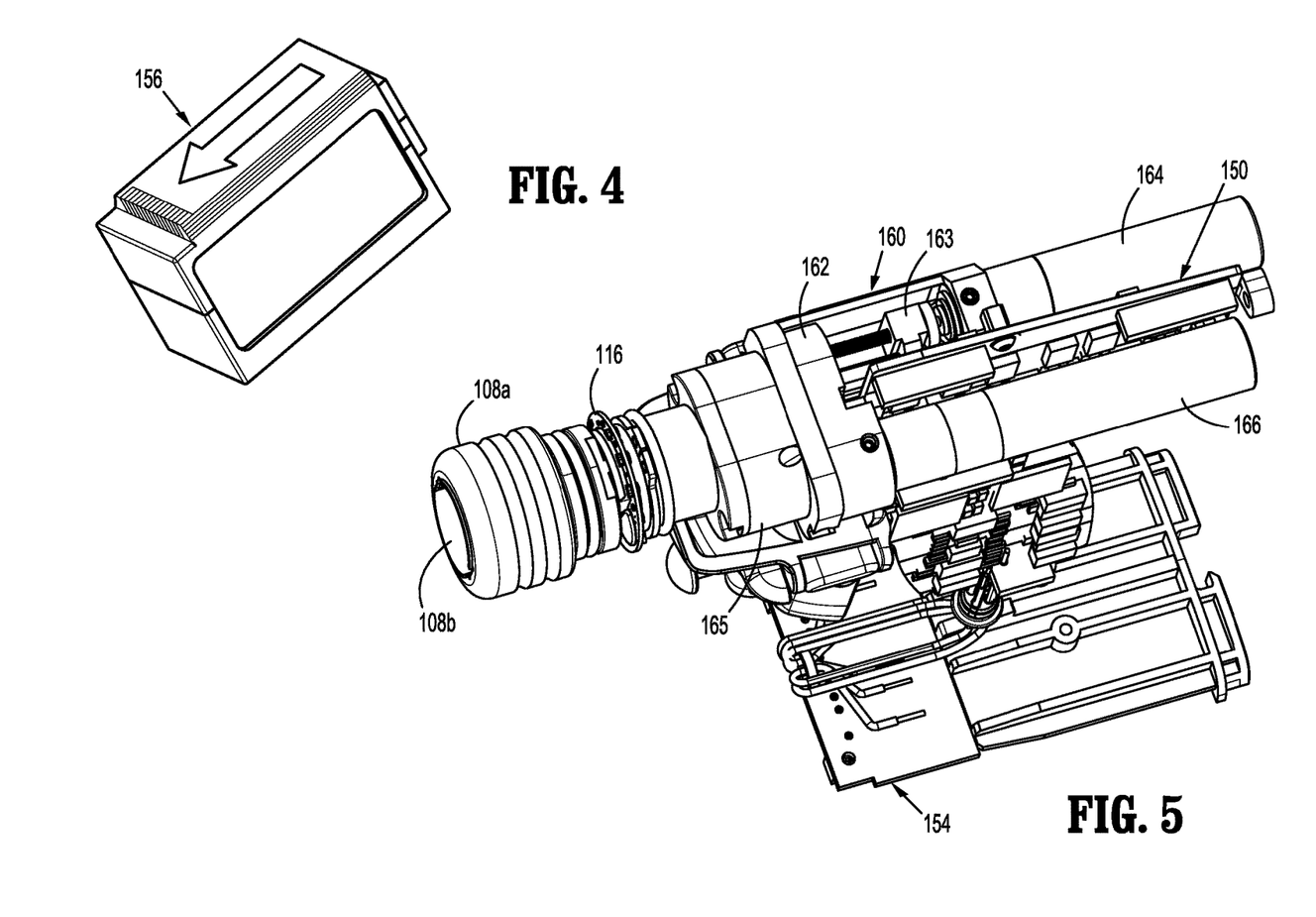
FIG. 4 is a perspective view of a battery of the surgical instrument of FIG. 1, according to the present disclosure.
FIG. 5 is a top, partially-disassembled view of the surgical instrument of FIG. 1, according to the present disclosure.

With reference to FIGS. 3 and 5, distal half-section 110a of upper housing portion 108 defines a nose or connecting portion 108a. A nose cone 114 is supported on nose portion 108a of upper housing portion 108. Nose cone 114 is fabricated from a transparent material. The instrument 100 also includes a user interface device, such as an illumination member 116, which is disposed within nose cone 114 such that illumination member 116 is visible therethrough. Illumination member 116 is may be a light emitting diode printed circuit board (LED PCB). Illumination member 116 is configured to illuminate multiple colors with a specific color pattern being associated with a unique discrete event.

The instrument 100 may also include one or more audio outputs (e.g., tones, bells, buzzers, integrated speaker, etc.) to communicate various status changes to the user such as lower battery, empty cartridge, etc. The audible feedback can be used in conjunction with or in lieu of the illumination member 116. The audible feedback may be provided in the forms of clicks, snaps, beeps, rings and buzzers in single or multiple pulse sequences. In one embodiment, a simulated mechanical sound may be prerecorded which replicates the click and/or snap sounds generated by mechanical lockouts and mechanisms of conventional non-powered instruments. This eliminates the need to generate such mechanical sounds through the actual components of the instrument 100 and also avoids the use of beeps and other electronic sounds which are usually associated with other operating room equipment, thereby preventing confusion from extraneous audible feedback.

The instrument 100 may also provide for haptic or vibratory feedback through a haptic mechanism (not explicitly shown). The haptic feedback may be used in conjunction with the auditory and visual feedback or in lieu thereof to avoid confusion with the operating room equipment, which relies on audio and visual feedback. The haptic mechanism may be an asynchronous motor that vibrates in a pulsating manner. In one embodiment, the vibrations are at a frequency of about 30 Hz or above providing a displacement having an amplitude of 1.5 mm or lower to limit the vibratory effects from the end effector 300.

In further embodiments, the instrument 100 may include any other suitable user interface device including, but not limited to, display devices, (e.g., liquid crystal displays, organic light-emitting displays, electrophoretic ink displays, etc.).

Upper housing portion 108 of handle housing 102 provides a housing in which drive mechanism 160 is situated. As illustrated in FIG. 5, drive mechanism 160 is configured to drive shafts and/or gear components in order to perform the various operations of surgical instrument 100. In particular, drive mechanism 160 is configured to drive shafts and/or gear components in order to selectively move tool assembly 304 of end effector 300 (see FIGS. 1 and 9) relative to proximal body portion 302 of end effector 300, to rotate end effector 300 about a longitudinal axis "X" (see FIG. 2) relative to handle housing 102, to move anvil assembly 306 relative to cartridge assembly 308 of end effector 300, and/or to fire a stapling and cutting cartridge within cartridge assembly 308 of end effector 300.

The drive mechanism 160 includes a selector gearbox assembly 162 that is located immediately proximal relative to adapter 200. Proximal to the selector gearbox assembly 162 is a function selection module 163 having a first motor 164 that functions to selectively move gear elements within the selector gearbox assembly 162 into engagement with an input drive component 165 having a second motor 166. The motor 164 may be any electrical motor configured to actuate one or more drives (e.g., rotatable drive connectors 118, 120, 122 of FIG. 6). The motor 164 is coupled to the power source 156, which may be a DC battery (e.g., rechargeable lead-based, nickel-based, lithium-ion based, battery etc.), an AC/DC transformer, or any other power source suitable for providing electrical energy to the motor 164.

As illustrated in FIGS. 1-4, and as mentioned above, distal half-section 110a of upper housing portion 108 defines a connecting portion 108a configured to accept a corresponding drive coupling assembly 210 of adapter 200.

Figure 6:
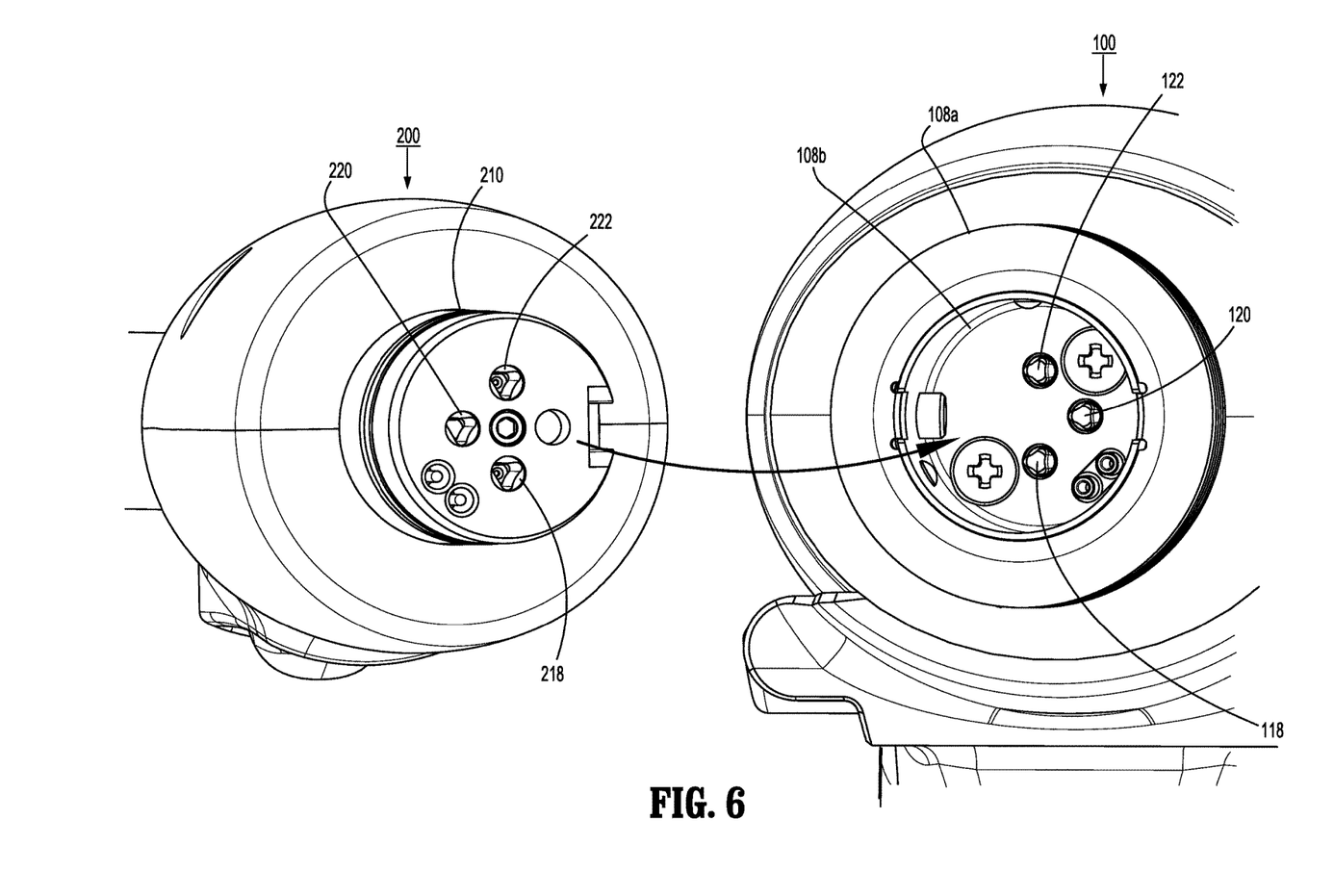
FIG. 6 is a front, perspective view of the surgical instrument of FIG. 1 with the adapter separated therefrom, according to the present disclosure.
Figure 7:
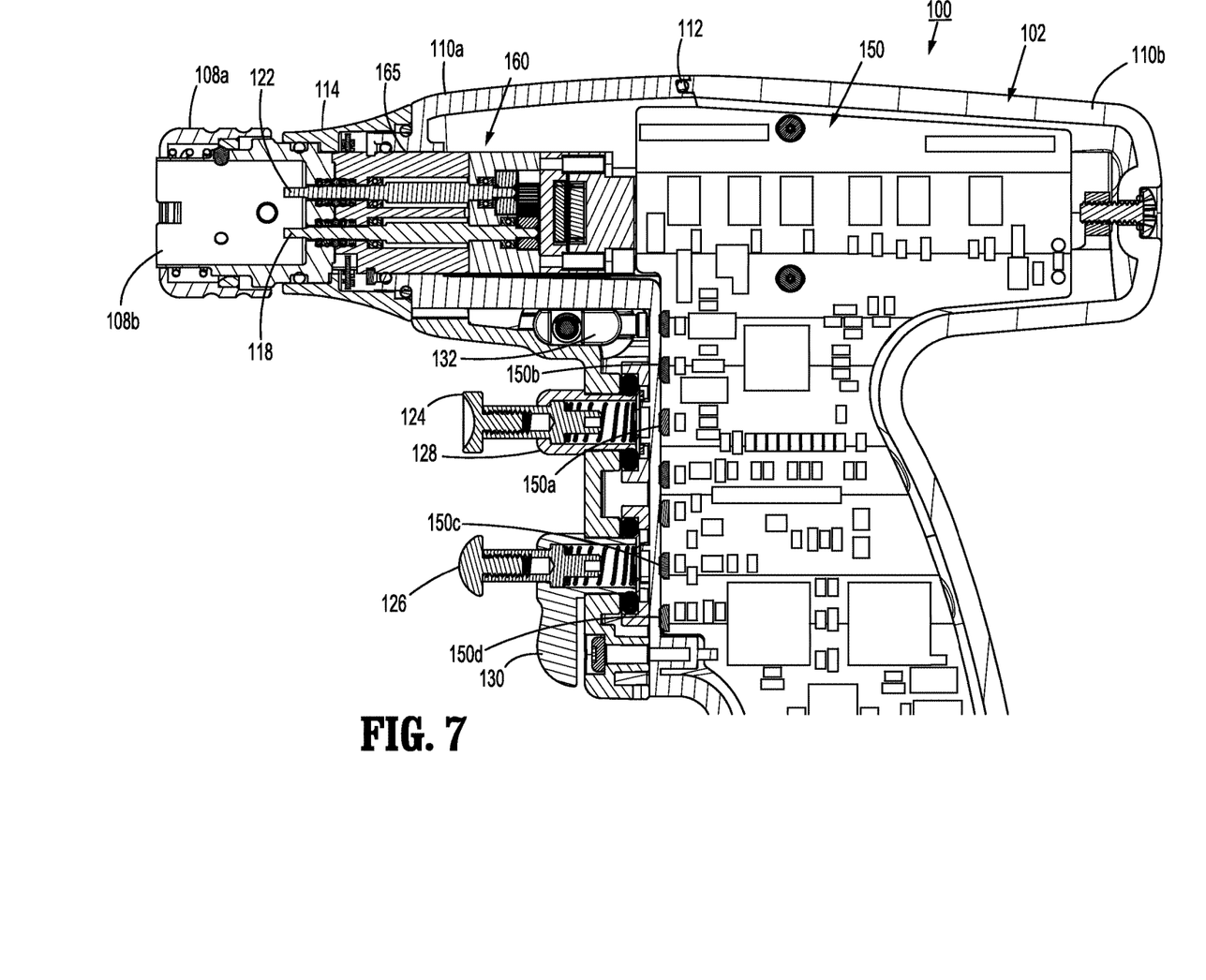
FIG. 7 is a side, cross-sectional view of the surgical instrument of FIG. 1, as taken through 7-7 of FIG. 2, according to the present disclosure.
Figure 8:
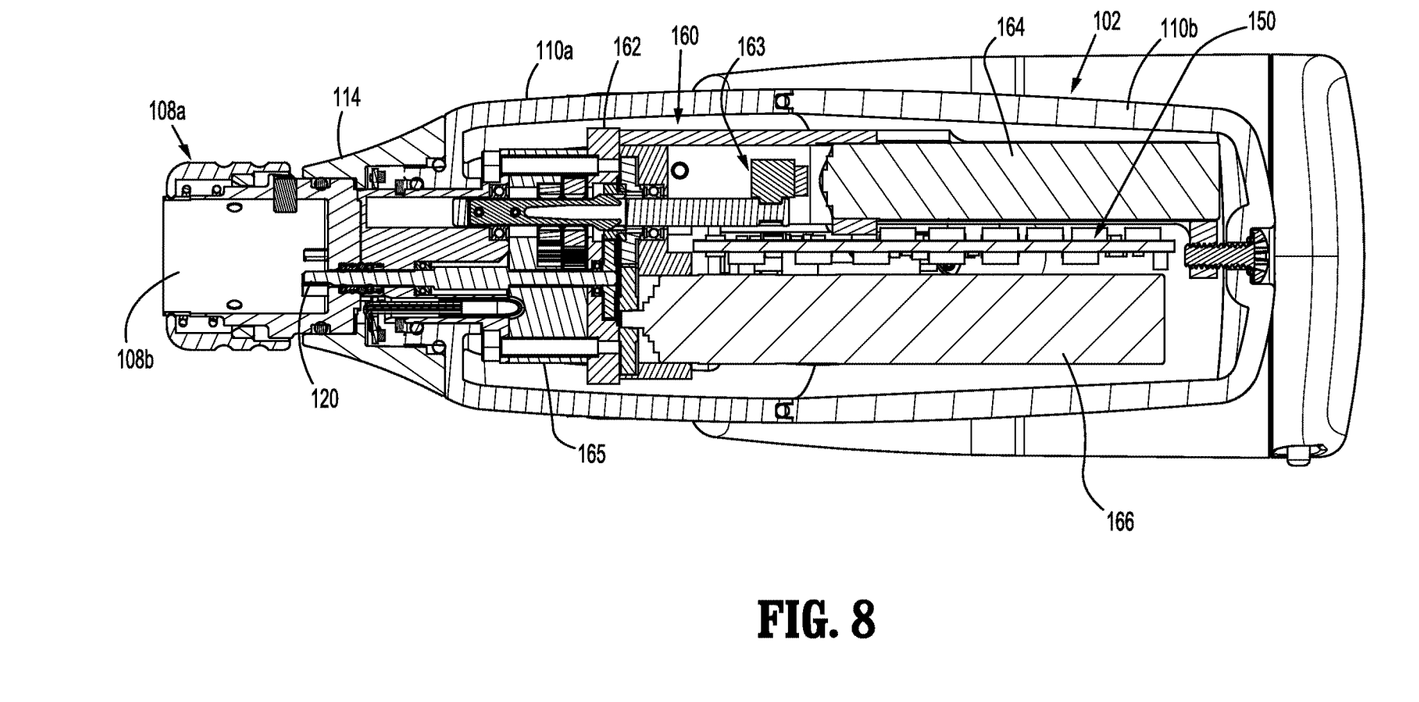
FIG. 8 is a top, cross-sectional view of the surgical instrument of FIG. 1, as taken through 8-8 of FIG. 2, according to the present disclosure.

As illustrated in FIGS. 6-8, connecting portion 108a of surgical instrument 100 has a cylindrical recess 108b that receives a drive coupling assembly 210 of adapter 200 when adapter 200 is mated to surgical instrument 100. Connecting portion 108a houses three rotatable drive connectors 118, 120, 122.

When adapter 200 is mated to surgical instrument 100, each of rotatable drive connectors 118, 120, 122 of surgical instrument 100 couples with a corresponding rotatable connector sleeve 218, 220, 222 of adapter 200 as shown in FIG. 6. In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical instrument 100 causes a corresponding rotation of the corresponding connector sleeve 218, 220, 222 of adapter 200.

The mating of drive connectors 118, 120, 122 of surgical instrument 100 with connector sleeves 218, 220, 222 of adapter 200 allows rotational forces to be independently transmitted via each of the three respective connector interfaces. The drive connectors 118, 120, 122 of surgical instrument 100 are configured to be independently rotated by drive mechanism 160. In this regard, the function selection module 163 of drive mechanism 160 selects which drive connector or connectors 118, 120, 122 of surgical instrument 100 is to be driven by the input drive component 165 of drive mechanism 160.

Since each of drive connectors 118, 120, 122 of surgical instrument 100 has a keyed and/or substantially non-rotatable interface with respective connector sleeves 218, 220, 222 of adapter 200, when adapter 200 is coupled to surgical instrument 100, rotational force(s) are selectively transferred from drive mechanism 160 of surgical instrument 100 to adapter 200.

The selective rotation of drive connector(s) 118, 120 and/or 122 of surgical instrument 100 allows surgical instrument 100 to selectively actuate different functions of end effector 300. As will be discussed in greater detail below, selective and independent rotation of first drive connector 118 of surgical instrument 100 corresponds to the selective and independent opening and closing of tool assembly 304 of end effector 300, and driving of a stapling/cutting component of tool assembly 304 of end effector 300. Also, the selective and independent rotation of second drive connector 120 of surgical instrument 100 corresponds to the selective and independent articulation of tool assembly 304 of end effector 300 transverse to longitudinal axis "X" (see FIG. 2). Additionally, the selective and independent rotation of third drive connector 122 of surgical instrument 100 corresponds to the selective and independent rotation of end effector 300 about longitudinal axis "X" (see FIG. 2) relative to handle housing 102 of surgical instrument 100.

As mentioned above and as illustrated in FIGS. 5 and 8, drive mechanism 160 includes a selector gearbox assembly 162; and a function selection module 163, located proximal to the selector gearbox assembly 162, that functions to selectively move gear elements within the selector gearbox assembly 162 into engagement with second motor 166. Thus, drive mechanism 160 selectively drives one of drive connectors 118, 120, 122 of surgical instrument 100 at a given time.

As illustrated in FIGS. 1-3, handle housing 102 supports a control assembly 107 on a distal surface or side of intermediate housing portion 108. The control assembly 107 is a fully-functional mechanical subassembly that can be assembled and tested separately from the rest of the instrument 100 prior to coupling thereto.

Control assembly 107, in cooperation with intermediate housing portion 108, supports a pair of finger-actuated control buttons 124, 126 and a pair rocker devices 128, 130 within a housing 107a. The control buttons 124, 126 are coupled to extension shafts 125, 127 respectively. In particular, control assembly 107 defines an upper aperture 124a for slidably receiving the extension shaft 125, and a lower aperture 126*a* for slidably receiving the extension shaft 127.

Reference may be made to a commonly-owned U.S. patent application Ser. No. 13/331,047, the entire contents of which are incorporated by reference herein, for a detailed discussion of the construction and operation of the surgical instrument 100.

Figure 9:
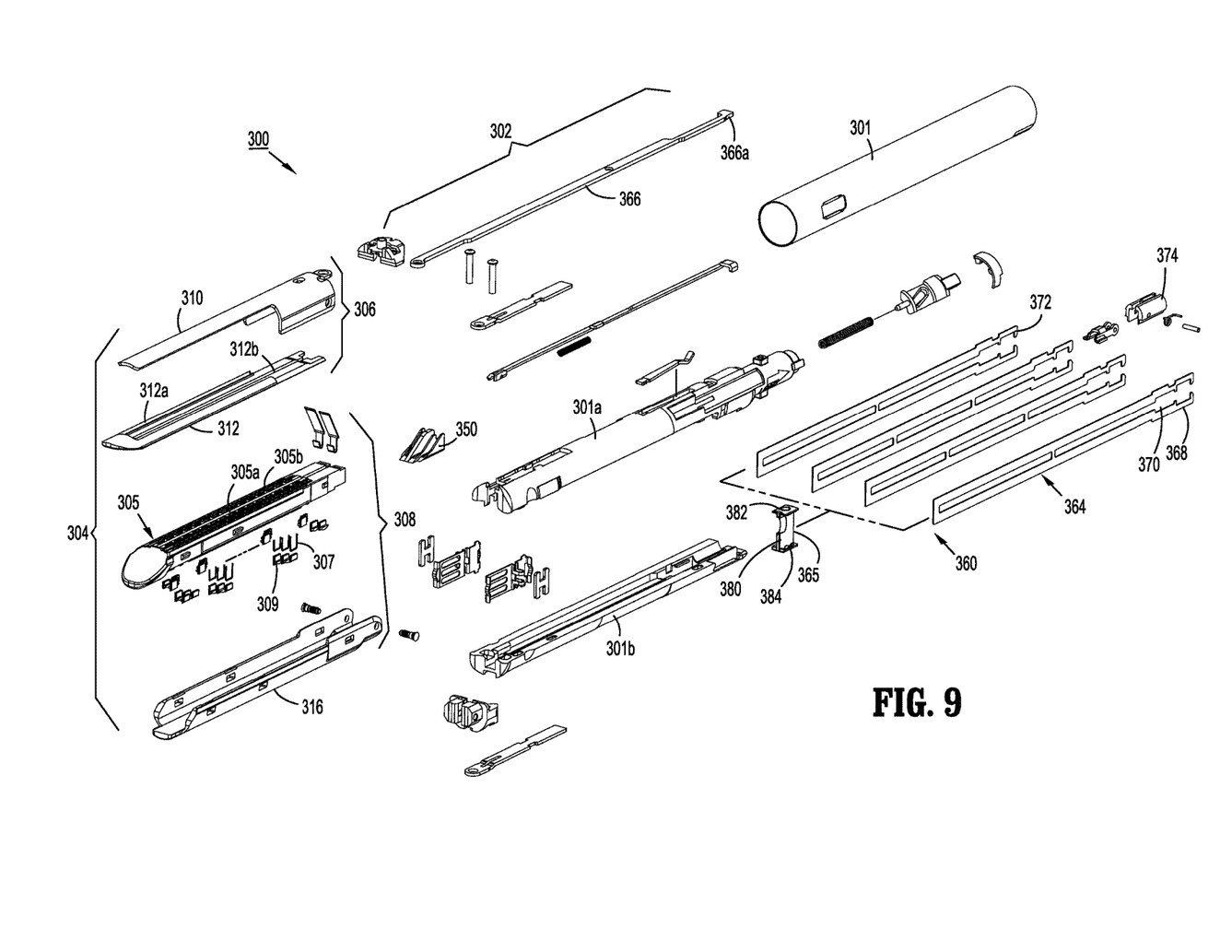
FIG. 9 is a perspective, exploded view of an end effector of FIG. 1, according to the present disclosure.

Referring to FIG. 9, drive assembly 360 of end effector 300 includes a flexible drive shaft 364 having a distal end which is secured to a drive beam 365, and a proximal engagement section 368. Engagement section 368 includes a stepped portion defining a shoulder 370. A proximal end of engagement section 368 includes diametrically opposed inwardly extending fingers 372. Fingers 372 engage a hollow drive member 374 to fixedly secure drive member 374 to the proximal end of shaft 364. Drive member 374 defines a proximal porthole, which receives a connection member of drive tube 246 (FIG. 1) of adapter 200 when end effector 300 is attached to distal coupling 230 of adapter 200.

The drive beam 365 includes a cam member 382 and a catch 384 disposed on top and bottom of a vertical support strut 380, respectively. Cam member 382 is dimensioned and configured to engage and translate with respect to an exterior camming surface 312*a* of anvil plate 312 to progressively clamp the anvil against body tissue during firing.

When drive assembly 360 is advanced distally within tool assembly 304, the cam member 380 of drive beam 365 moves within a channel 312*b* defined within the anvil plate 312 and a corresponding longitudinal slot (not shown) formed on an underside of the anvil cover 310. The support strut 380 moves within a channel 305*a* of the staple cartridge 305 and the catch 384 moves over the exterior surface of carrier 316 to close tool assembly 304 and fire staples therefrom.

Proximal body portion 302 of end effector 300 includes a sheath or outer tube 301 enclosing an upper housing portion 301*a* and a lower housing portion 301*b*. The housing portions 301*a* and 301*b* enclose an articulation link 366 having a hooked proximal end 366*a* which extends from a proximal end of end effector 300. Hooked proximal end 366*a* of articulation link 366 engages a coupling hook (not shown) of adapter 200 when end effector 300 is secured to distal housing 232 of adapter 200. When drive bar (not shown) of adapter 200 is advanced or retracted as described above, articulation link 366 of end effector 300 is advanced or retracted within end effector 300 to pivot tool assembly 304 in relation to a distal end of proximal body portion 302.

As illustrated in FIG. 9 above, cartridge assembly 308 of tool assembly 304 includes a staple cartridge 305 supportable in carrier 316. Staple cartridge 305 defines a central longitudinal slot 305*a*, and three linear rows of staple retention slots 305*b* positioned on each side of longitudinal slot 305*a*. Each of staple retention slots 305*b* receives a single staple 307 and a portion of a staple pusher 309. During operation of instrument 100, drive assembly 360 abuts an actuation sled 350 and pushes actuation sled 350 through cartridge 305. As the actuation sled moves through cartridge 305, cam wedges of the actuation sled 350 sequentially engage staple pushers 309 to move staple pushers 309 vertically within staple retention slots 305*b* and sequentially eject a single staple 307 therefrom for formation against anvil plate 312. The staple cartridge 305 may be replaceable allowing for reuse of the end effector 300 with multiple staple cartridges 305 and/or selecting fasteners of suitable size, which may be from about 1 mm to about 20 mm.

Figure 10:
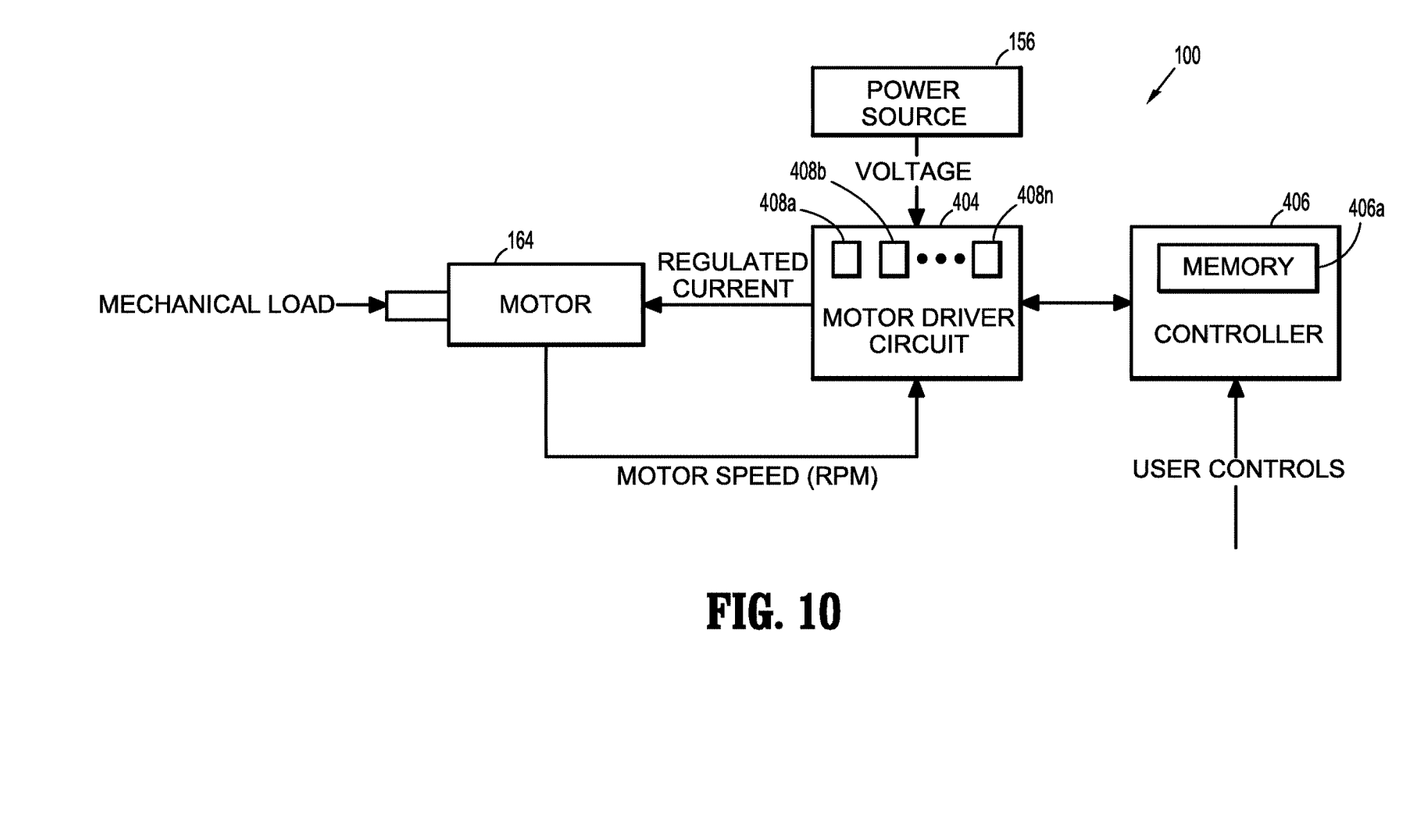
FIG. 10 is a schematic diagram of the surgical instrument of FIG. 1 according to the present disclosure.

With reference to FIG. 10, the power source 156 and the motor 164 are coupled to a motor driver circuit 404 disposed on the circuit board 154 which controls the operation of the motor 164 including the flow of electrical energy from the power source 156 to the motor 164. The driver circuit 404 includes a plurality of sensors 408*a*, 408*b*, . . . 408*n* configured to measure operational states of the motor 164 and the power source 156. The sensors 408*a*-*n* may include voltage sensors, current sensors, temperature sensors, telemetry sensors, optical sensors, and combinations thereof. The sensors 408*a*-408*n* may measure voltage, current, and other electrical properties of the electrical energy supplied by the power source 156. The sensors 408*a*-408*n* may also measure rotational speed as revolutions per minute (RPM), torque, temperature, current draw, and other operational properties of the motor 164. RPM may be determined by measuring the rotation of the motor 164. Position of various drive shafts (e.g., rotatable drive connectors 118, 120, 122 of FIG. 6) may be determined by using various linear sensors disposed in or in proximity to the shafts or extrapolated from the RPM measurements. In embodiments, torque may be calculated based on the regulated current draw of the motor 164 at a constant RPM. In further embodiments, the driver circuit 404 and/or the controller 406 may measure time and process the above-described values as a function thereof, including integration and/or differentiation, e.g., to determine the change in the measured values and the like.

The driver circuit 404 is also coupled to a controller 406, which may be any suitable logic control circuit adapted to perform the calculations and/or operate according to a set of instructions described in further detail below. The controller 406 may include a central processing unit operably connected to a memory which may include transitory type memory (e.g., RAM) and/or non-transitory type memory (e.g., flash media, disk media, etc.). The controller 406 includes a plurality of inputs and outputs for interfacing with the driver circuit 404. In particular, the controller 406 receives measured sensor signals from the driver circuit 404 regarding operational status of the motor 164 and the power source 156 and, in turn, outputs control signals to the driver circuit 404 to control the operation of the motor 164 based on the sensor readings and specific algorithm instructions, which are discussed in more detail below. The controller 406 is also configured to accept a plurality of user inputs from a user interface (e.g., switches, buttons, touch screen, etc. of the control assembly 107 coupled to the controller 406).

The instrument 100 and the method according to the present disclosure may be utilized with any other powered surgical instrument, including, but not limited to, linear powered staplers, circular or arcuate powered staplers, graspers, electrosurgical sealing forceps, rotary tissue blending devices, and the like. The instrument 100 and the method according to the present disclosure provide for determining one or more tissue properties and providing an output indicative of a suitable end effector for treating tissue. The instrument 100 may be coupled to a test unit, which may be a test end effector 400 and/or a test cartridge 405. The test cartridge 405 may be used with the end effector 300 or the test end effector 400. The test unit is configured to be operable by the instrument 100 to determine one or more tissue properties, e.g., thickness. The instrument 100 may output the determine tissue property and/or provide one or more suitable end effectors 300 and/or staple cartridges 305 for treating tested tissue.

Figure 11:
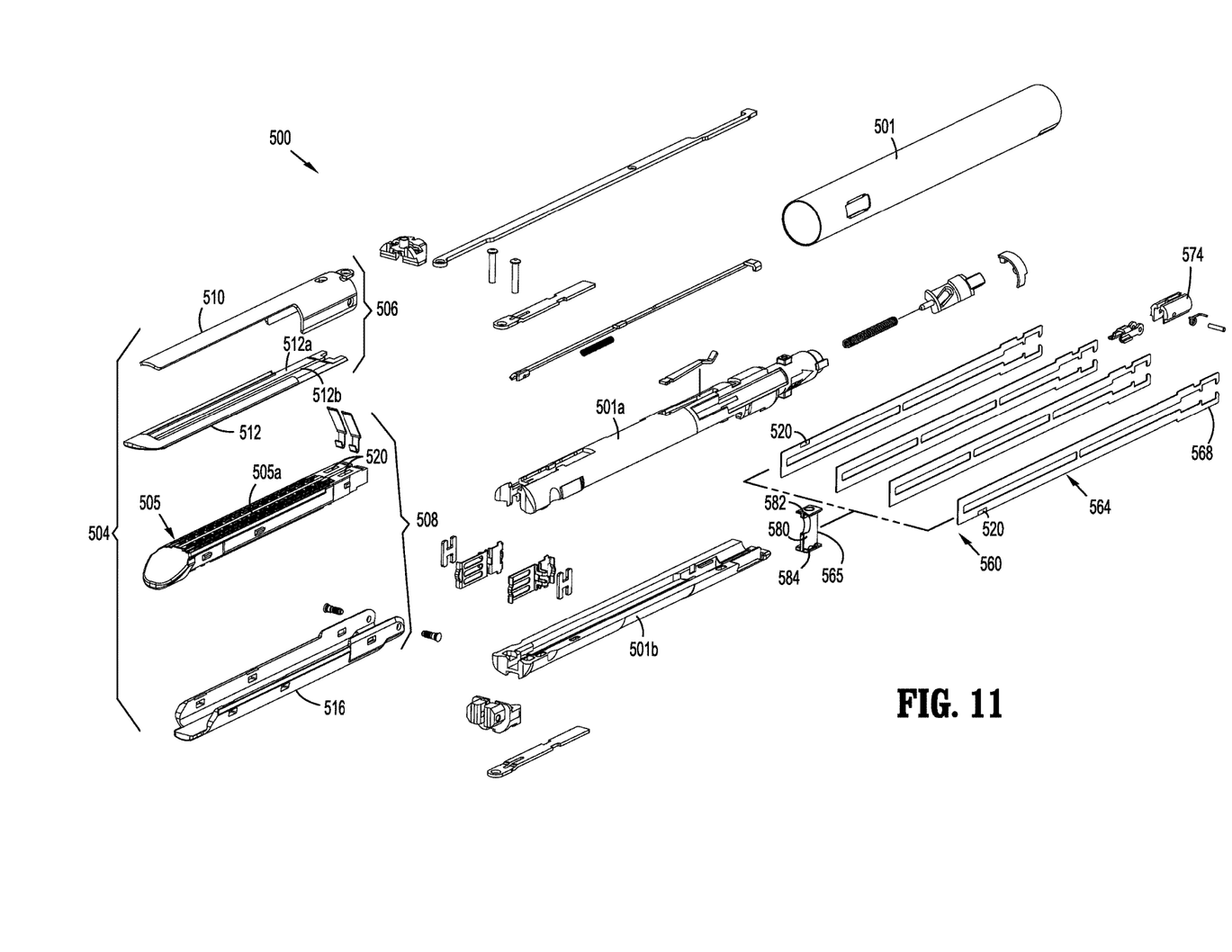
FIG. 11 is a perspective, exploded view of a test end effector and test cartridge, according to the present disclosure.

With reference to FIG. 11, the test end effector 500 with the test cartridge 505 is shown. In embodiments, the test end effector 500 and the test cartridge 505 may be used to measure tissue properties either alone or in combination. The test end effector 500 is substantially similar to the end effector 300 and includes an anvil assembly 506 movable relative to a cartridge assembly 508 and a drive assembly 560 having a flexible drive shaft 564. The drive shaft 564 includes a distal end which is secured to a drive beam 565, and a proximal engagement section 568, which engages a hollow drive member 574, which in turn receives a connection member of drive tube 246 (FIG. 1) of adapter 200 when end effector 500 is attached to distal coupling 230 of adapter 200.

The drive beam 565 includes a cam member 582 and a catch 584 disposed on top and bottom of a vertical support strut 580, respectively. Cam member 582 is dimensioned and configured to engage and translate with respect to an exterior camming surface 512a of anvil plate 512 to progressively clamp the anvil against body tissue during firing.

When drive assembly 560 is advanced distally within tool assembly 504, the cam member 580 of drive beam 565 moves within a channel 512b defined within the anvil plate 512 and a corresponding longitudinal slot (not shown) formed on an underside of the anvil cover 510. The support strut 580 moves within a channel 505a of the test cartridge 505 and the catch 584 moves over the exterior surface of carrier 516 to close tool assembly 504. The test end effector 500 also includes a sheath or outer tube 501 enclosing an upper housing portion 501a and a lower housing portion 501b.

The test end effector 500 also includes a cartridge assembly 508 configured to house the test cartridge 505, which is supportable within carrier 516. Test cartridge 505 also defines a central longitudinal slot 505a.

Since the test end effector 500 is used to measure tissue properties it may be devoid of certain components, such as an articulation link 366 and/or the actuation sled 350 (FIG. 9), to minimize the cost and complexity of the end effector 300. Similarly, the test cartridge 505 may be devoid of any tissue fasteners to prevent accidental clamping of tissue. In embodiments, the channel 512b defined within the anvil plate 512 and/or the central longitudinal slot 505a of the test cartridge 505 may be shorter than the counterpart channel 312b defined within the anvil plate 312 and/or the central longitudinal slot 305a of the staple cartridge 305. This is due to the fact that the distance travelled by the drive beam 565 to close the tool assembly 504 may be shorter than the distance for ejecting staples 307 out of the staple cartridge 305.

The test end effector 500 and/or the test cartridge 505 may include one or more sensors 520 coupled to any of the components actuated to close the tool assembly 504. In embodiments, the sensors 520 may be disposed on the inner surfaces of the anvil assembly 506 and/or cartridge assembly 508. In further embodiments, the sensors 520 may be coupled to the drive assembly 560.

The sensors 520 may be any suitable sensors that determine the amount of mechanical force being applied thereto, which corresponds to the amount of force being applied to the tissue being clamped. In particular, the sensors 520 detect the force being applied to the tissue and transmit the electrical signals indicative of the force to the controller 406, which then derives tissue compression. The sensors 520 may be coupled to the controller 406 of the instrument 100 using a wireless (e.g., RFID, Bluetooth™, etc.) or wired connection (e.g., 2-wire bus).

Suitable sensors 520 may include, and are not limited to, force transducers, piezoelectric elements, piezoresistive elements, load cells, metal film strain gauges, semiconductor strain gauges, inductive pressure sensors, capacitive pressure sensors, potentiometric pressure transducers, and combinations thereof.

In embodiments, sensors 520 may also include proximity sensors for determining a gap distance between the anvil assembly 506 and the cartridge assembly 508. Suitable sensors 520 include, but are not limited to, potentiometers, linear variable differential transformers, magneto-resistive elements, capacitive elements, electromagnetic induction sensors, Hall effect sensors, and combinations thereof.

In further embodiments, sensor 520 may include electrical and/or optical sensors for determining additional properties including, but not limited to, tissue impedance, tissue translucency/opacity, tissue hydrology, tissue, vascularity, burst strength of sealed vessels, tissue seal fusion, temperature, depth of tissue penetration with applied treatment energy, thermal spread, and combinations thereof. Suitable electrical and/or optical sensors include electrodes, optical transmitters (e.g., LEDs), which irradiate tissue, photoreceptors, and the like.

During use, the test end effector 500 is coupled to the instrument 100 via the adapter 200. In embodiments, the test cartridge 505 may be coupled to the carrier 316 of the end effector 300 or the carrier 516 of the test end effector 500. Once the test end effector 500 and/or the test cartridge 505 are coupled to the instrument 100, the controller 406 identifies the test end effector 500 and/or the test cartridge 505 as well as the sensors 520 housed therein. In response to detecting the test end effector 500 and/or the test cartridge 505, the controller 406 configures the instrument 100 into a testing mode. The instrument 100 is then used to clamp tissue using the test end effector 500 and/or the test cartridge 505. The sensors 520 housed within the test end effector 500 and/or the test cartridge 505 measure the force exerted on end effector 300 or end effector 500 as well as any other tissue properties described above. The sensor measurements are transmitted to the controller 406, which then determines the force applied to the tissue based on the measurements from the sensors 520 as well as any other tissue properties.

The controller 406 is further configured to determine one or more suitable end effectors 300 for treating tissue based on the measured tissue properties. The memory of the controller 406 may store a look-up table storing a list of end effectors 300 and corresponding clamping force or other tissue type. The controller 406 selects the end effector 300 based on the measured clamping force or other sensed measurement.

The instrument 100 may output the suitable type of the end effector 300 through the illumination member 116 or other feedback device described above (e.g., audio tone). The illumination member 116 may indicate the suitable end effector 300 by using predetermined color, flashing patterns, and combinations thereof, which are correlated to the end effectors 300. In particular, each type of the end effector 300 may be designated by a predetermined color or identification number, such that the output of the illumination member 116 is used to indicate the suitable type of the end effector 300. In embodiments, multiple end effectors 300 may be suitable for treating tissue, such that the illumination member 116 outputs multiple indications. This allows the practitioner to select from among a plurality of suitable end effectors 300.

It should be understood that the foregoing description is only illustrative of the present disclosure. Various alternatives and modifications can be devised by those skilled in the art without departing from the disclosure. For example, an instrument of the present invention can be used in a training method to teach surgeons end effector selection, the end effectors then being used on a manual type device, such a surgical stapler. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical instrument, comprising:
    a test end effector devoid of fasteners and including a test jaw assembly including:
        a pair of jaws configured to clamp about tissue; and
        a sensor configured to measure a force exerted on the pair of jaws; and
    a handle assembly configured to couple to the test end effector, the handle assembly including:
        a drive assembly;
        a motor operatively coupled to the drive assembly;
        a controller operatively coupled to the motor, the controller configured to identify whether the test end effector is coupled to the handle assembly, to control operation of the motor to actuate the test end effector to measure the force, and to select, based on the force a subset plurality of suitable treatment end effectors from a plurality of treatment end effectors; and
        a user interface device coupled to the controller, the user interface configured to display an indicia corresponding to the subset plurality of suitable treatment end effectors.

2. The surgical instrument according to claim 1, wherein the sensor is selected from the group consisting of force transducers, piezoelectric elements, piezoresistive elements, load cells, metal film strain gauges, semiconductor strain gauges, inductive pressure sensors, capacitive pressure sensors, potentiometric pressure transducers, and combinations thereof.

3. The surgical instrument according to claim 1, wherein the user interface device is selected from the group consisting of a light emitting diode, an audio device, a display, and combinations thereof.

4. The surgical instrument according to claim 1, wherein the controller is further configured to identify the sensor.

5. A surgical system, comprising:
    a test end effector devoid of fasteners and including a test jaw assembly including:
        a pair of jaws configured to clamp about tissue; and
        a sensor configured to measure a force exerted on the pair of jaws; and
    a plurality of treatment end effectors, each of the treatment end effectors including a jaw assembly having a pair of jaws configured to clamp about tissue; and
    a handle assembly configured to selectively couple to at least one of the treatment end effector or the test end effector, the handle assembly including:
        a drive assembly;
        a motor operatively coupled to the drive assembly;
        a controller operatively coupled to the motor, the controller configured to identify whether the test end effector is coupled to the handle assembly, to control operation of the motor to actuate the test end effector to measure the force, and to select a subset plurality of suitable treatment end effectors from the plurality of treatment end effectors based on the force and
        a user interface device coupled to the controller, the user interface configured to display an indicia corresponding to the subset plurality of suitable treatment end effectors selected by the controller.

6. The surgical system according to claim 5, wherein the sensor is selected from the group consisting of force transducers, piezoelectric elements, piezoresistive elements, load cells, metal film strain gauges, semiconductor strain gauges, inductive pressure sensors, capacitive pressure sensors, potentiometric pressure transducers, and combinations thereof.

7. The surgical system according to claim 5, wherein the user interface device is selected from the group consisting of a light emitting diode, an audio device, a display, and combinations thereof.

8. The surgical system according to claim 7, wherein the user interface device outputs an indicia corresponding to the subset plurality of suitable treatment end effectors.

9. A method for treating tissue, comprising:
    coupling a test end effector including a pair of jaws to a handle assembly, the test end effector unable to fire a fastener and including a sensor configured to measure a force exerted on the pair of jaws;
    identifying, via a controller of the handle assembly, whether the test end effector is coupled to the handle assembly and the sensor;
    actuating the test end effector to measure the force;
    selecting, via the controller, a subset plurality of suitable treatment end effectors from a plurality of treatment end effectors based on the force; and
    indicating the subset plurality of suitable treatment end effectors on a user interface of the handle assembly.

10. The method according to claim 9, wherein indicating on the user interface includes outputting an indicia corresponding to the subset plurality of suitable treatment end effectors, wherein indicia is selected from the group consisting of a color, an identification number, an audio tone, and combinations thereof.

11. The method according to claim 9, further comprising:
    coupling a selected treatment end effector of the subset plurality of suitable treatment end effectors to the handle assembly; and
    clamping tissue with the selected treatment end effector from the subset plurality of suitable treatment end effectors.

* * * * *